United States Patent
Bartl et al.

(10) Patent No.: US 7,446,116 B2
(45) Date of Patent: Nov. 4, 2008

(54) MONTELUKAST AMANTADINE SALT

(75) Inventors: Jiri Bartl, Strelice (CZ); Frantisek Picha, Brno (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 11/687,437

(22) Filed: Mar. 16, 2007

(65) Prior Publication Data

US 2007/0225326 A1  Sep. 27, 2007

Related U.S. Application Data

(60) Provisional application No. 60/783,027, filed on Mar. 17, 2006.

(51) Int. Cl.
*A61K 31/47* (2006.01)
*C07D 215/14* (2006.01)
*C07D 215/18* (2006.01)

(52) U.S. Cl. ........................ 514/311; 546/174

(58) Field of Classification Search ............... 514/311; 546/180, 174
See application file for complete search history.

(56) References Cited

U.S. PATENT DOCUMENTS

| | | | |
|---|---|---|---|
| 5,266,568 A | 11/1993 | Belley et al. | |
| 5,270,324 A | 12/1993 | Zamboni et al. | |
| 5,523,477 A | 6/1996 | King et al. | |
| 5,565,473 A * | 10/1996 | Belley et al. | 514/313 |
| 5,585,115 A | 12/1996 | Sherwood et al. | |
| 5,614,632 A | 3/1997 | Bhupathy et al. | |
| 5,856,322 A | 1/1999 | Belley et al. | |
| 5,869,673 A | 2/1999 | Tung et al. | |
| 6,063,802 A | 5/2000 | Winterborn | |
| 6,320,052 B1 | 11/2001 | Bhupathy et al. | |
| 2004/0265375 A1 | 12/2004 | Platteeuw et al. | |
| 2005/0107426 A1 | 5/2005 | Overeem et al. | |
| 2005/0107612 A1 | 5/2005 | Reguri et al. | |
| 2005/0187243 A1 | 8/2005 | Niddam-Hildesheim et al. | |
| 2005/0234241 A1 | 10/2005 | Sundaram et al. | |
| 2005/0245568 A1 | 11/2005 | Overeem et al. | |
| 2005/0245569 A1 | 11/2005 | Overeem et al. | |
| 2006/0004204 A1 * | 1/2006 | Reguri et al. | 546/177 |
| 2008/0004204 A1 | 1/2008 | Reguri et al. | |

FOREIGN PATENT DOCUMENTS

| | | |
|---|---|---|
| CN | 1420113 A | 5/2003 |
| EP | 0 480 717 | 4/1992 |
| WO | WO 95/18107 | 7/1995 |
| WO | WO 03/066598 A1 | 8/2003 |
| WO | WO 2004/108679 | 12/2004 |
| WO | WO 2005/074935 | 8/2005 |

OTHER PUBLICATIONS

Norris, Experimental Organic Chemistry, McGraw-Hill, 1924, pp. 3-9, 21-25, and 29-31.*
"An Efficient Synthesis of LTD$_4$ Antagonist L-699,392" by A.O. King et al., *J. Org. Chem.* 1993, 58, pp. 3731-3735.

* cited by examiner

*Primary Examiner*—Bernard Dentz
*Assistant Examiner*—David E Gallis
(74) *Attorney, Agent, or Firm*—Mark R. Buscher

(57) ABSTRACT

An amantadine salt of montelukast is useful in purification of montelukast or its salts and as a pharmaceutical active ingredient.

19 Claims, No Drawings

MONTELUKAST AMANTADINE SALT

This application claims the benefit of priority under 35 U.S.C. § 119(e) from U.S. provisional patent application Ser. No. 60/783,027, filed Mar. 17, 2006; the entire contents of which are incorporated herein by reference.

BACKGROUND OF THE INVENTION

The present invention relates to an amantadine salt of montelukast and the uses thereof.

EP 480717 discloses certain substituted quinoline compounds including [R-(E)]-1-[[[1-[3-[2-[7-chloro-2-quinolinyl] ethenyl]phenyl]-3-[2-(1-hydroxy-1-methylethyl) phenyl] propyl] thio] methyl] cyclopropaneacetic acid sodium salt (now more commonly known as, and referred to herein as montelukast sodium) of the formula (1).

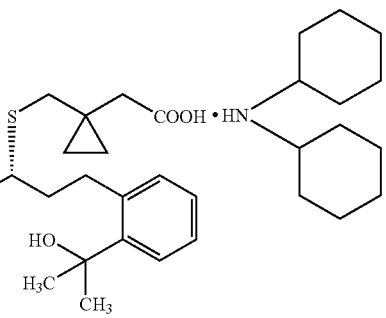

Montelukast sodium is a selective and orally active leukotriene receptor antagonist that inhibits the cysteinyl leukotriene CysLT1 receptor. It is useful as an anti-asthmatic, anti-allergic, anti-inflammatory and/or cytoprotective agent.

Montelukast sodium is indicated for the prophylaxis and chronic treatment of asthma in adults and pediatric patients 6 years of age and older. The dosage for adolescents and adults 15 years of age and older is typically one 10-mg tablet daily to be taken in the evening.

Montelukast sodium is a hygroscopic white to off-white powder, which is freely soluble in ethanol, methanol, and water and practically insoluble in acetonitrile.

The reported synthesis of montelukast sodium in EP 480717 proceeds through the corresponding methyl ester. The methyl ester of montelukast is hydrolyzed to the free acid (montelukast acid of the formula 2)

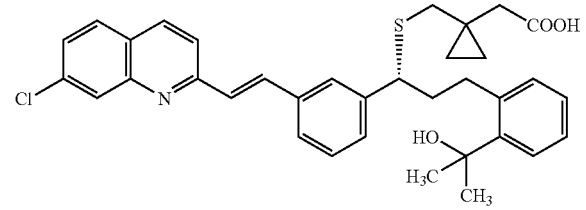

and the later converted directly to the corresponding sodium salt.

This process is not particularly suitable for large-scale production because it requires tedious chromatographic purification of the methyl ester intermediate and/or the final product, and the product yields are low.

WO Patent Application 95/18107 discloses an improved process for the preparation of crystalline montelukast sodium salt, which comprises the generation of a dilithium dianion of 1-(mercaptomethyl) cyclopropaneacetic acid followed by condensation with 2-(2-(3(S)-(3-(2-(7-chloro-2-quinolinyl) ethenyl)phenyl)-3-methanesulfonyloxypropyl)phenyl)-2-propanol to afford the montelukast acid which is then converted, via the dicyclohexyl amine salt of montelukast (formula 3),

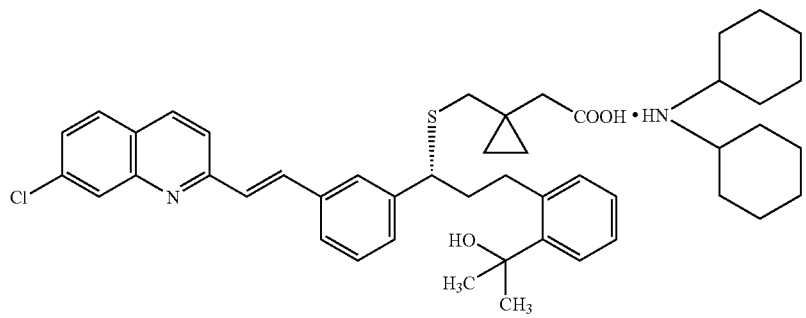

to its corresponding sodium salt. The obtained sodium salt is further crystallized from a mixture of toluene:acetonitrile to obtain crystalline montelukast sodium.

The montelukast dicyclohexyl amine salt is reported to be a useful intermediate for the purification of the crude montelukast acid before its conversion to the desired sodium salt. In the crystalline state, the montelukast dicyclohexylamine salt was obtained in two polymorphic modifications.

US Application Publication 2005-0107612 discloses a process for preparation of montelukast sodium comprising:
(i) providing a solution of starting montelukast free acid in a halogenated solvent, aromatic solvent, or mixtures thereof;
(ii) treating said solution with a source of sodium ion to convert said montelukast free acid into a sodium salt of montelukast;
(iii) adding a cyclic or acyclic hydrocarbon solvent to said solution thereby precipitating said sodium salt of montelukast.

It also teaches that montelukast acid may be generated in situ from an amine salt of montelukast, whereby specifically mentioned amines include tert. butylamine and phenyl ethylamine. The tert.butylamine salt of montelukast is described in example 6.

The tert.butylamine salt of montelukast is also described in US application 2005-0234241.

PCT patent application WO2004-108679 discloses another process wherein purification of montelukast proceeds via its dicyclohexylamine salt.

PCT patent application WO2005-074935 discloses several forms of montelukast free acid and a process for preparing montelukast free acid. The process generally includes a step of liberating montelukast free acid from its salt. One of the specifically mentioned salts (and the only amine salt) is dicyclohexylamine salt.

While the above disclosed amine salts of montelukast can be useful for isolation and purification of the montelukast acid before its conversion to montelukast sodium, it would be desirable to find another salt to facilitate the isolation and purification. Additionally, it would be desirable to find a pharmaceutically acceptable salt, as the known amine salts of montelukast suffer from the disadvantage that the amine moieties are generally not pharmaceutically acceptable.

SUMMARY OF THE INVENTION

The present invention relates to the discovery of amantadine salts of montelukast. Amantadine or more properly 1-aminoadamantane is a known pharmaceutical active ingredient and a salt formed with montelukast is thus pharmaceutically acceptable. Specifically, one aspect of the present invention relates to a montelukast salt of formula (4)

caused by certain psychiatric drugs. Furthermore, it is used to treat or prevent infections of the respiratory tract caused by a certain influenza virus, whereby it acts by slowing the growth of the virus. In medicinal practice, it is used as the hydrochloride salt, i.e., amantadine hydrochloride. As such, it is considered safe and nontoxic for a human patient at doses of at least 200 mg per day.

As used herein, "an amantadine salt of montelukast," and variations thereof, means any combination of amantadine ions and montelukast ions, whether in solid state such as a crystalline substance or dissolved in a solvent. It also includes all polymorphic and pseudo-polymorphic salts, if any, including hydrates, etc. Generally an amantadine montelukast salt can be represented by the formula (4). Typically the salt has

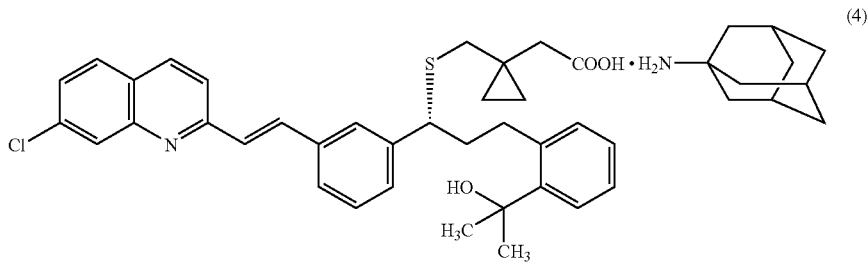

(4)

The salt can be in solid state, especially a crystalline form or state. The crystalline montelukast salt can have a high purity, such as when used as an intermediate for purifying and/or isolating montelukast acid or if used as an active agent directly, including purities of at least 95% and preferably at least 98%.

An additional aspect of the invention relates to a pharmaceutical composition comprising an amantadine salt of montelukast such as the montelukast salt of formula (4) and at least one pharmaceutically acceptable carrier and/or excipient. The composition can be a dosage form adapted for oral or nasal inhalation.

Another aspect of the invention relates to a process, which comprises: providing a solution containing montelukast, amantadine, and/or their ions in a solvent; and crystallizing an amantadine salt of montelukast from said solution. A preferred solvent is acetone.

A further aspect of the invention relates to a process for purification of montelukast or its salts, which comprises:
  synthesizing montelukast in a solution;
  adding amantadine to said solution;
  precipitating an amantadine salt of montelukast from said solution;
  recovering said amantadine salt of montelukast;
  optionally recrystallizing said amantadine salt of montelukast from a solvent; and
  converting said amantadine salt of montelukast into montelukast or its sodium salt.

DETAILED DESCRIPTION OF THE INVENTION

The 1-aminoadamantane is a well known compound which is useful, inter alia, in various pharmaceutical applications. Its generic name is amantadine and such name is generally used herein instead of 1-aminoadamantane. Amantadine is a biologically active compound as a dopamine agonist and is used to treat symptoms of Parkinson's disease and also side effects an approximately 1:1 molar ratio of montelukast to amantadine. It has been found that a montelukast amantadine salt can be readily isolated in solid, particularly crystalline form. An amantadine salt of montelukast can be formed by combining amantadine and montelukast in a solution. Typically the free base and the free acid, respectively, are used although it may be possible to use salt forms of either compound. Once a salt solution has been provided, that is a solution that contains montelukast, amantadine, and/or their ions in a solvent, a solid state amantadine salt can typically be easily crystallized/precipitated from the solution.

An amantadine salt may be used as a suitable intermediate in the synthesis of montelukast sodium, particularly as a tool for isolation and purification of the intermediate montelukast acid. Furthermore, an amantadine salt may be used as an active ingredient in montelukast-comprising medicaments.

Concerning the first aspect, the use of amantadine in making crystalline montelukast salt provides for an alternative method for isolating and/or purifying crude montelukast acid before its conversion to montelukast sodium. The known organic amines that have been used for this same purpose, i.e. the dicyclohexylamine or tert. butyl amine, are flammable, toxic and irritant liquids which are unstable in open air and of unpleasant smell. For instance, the tert.butyl amine boils already at about 45° C. and its toxicity, expressed as LD50 value in rats after oral administration is 44 mg/kg. Dicyclohexylamine is a high boiling flammable liquid with the LD50 toxicity of 373 mg/kg. Thus, in using them during chemical synthesis, special precautions may be necessary to protect the worker and the environment. To the contrary, amantadine is a stable solid compound of low toxicity (LD50 is 900 mg/kg) and of low irritation so that it can be handled with less difficulty.

The amantadine salt of montelukast may be precipitated quite easily in various solvents. Both starting components, the montelukast acid and the amantadine, are well soluble in these conventional solvents (listed below), but upon combining them a generally insoluble mutual salt is formed which precipitates from the solution. In general, the salt formation does not require heating and/or cooling of the solution to facilitate precipitation, but such an arrangement is not excluded.

The starting montelukast acid may be in an isolated form, and in such a case it is typically dissolved in the solvent prior to the treatment with amantadine, or it may be provided as part of a reaction mixture after the synthesis, e.g., a crude reaction mixture, a crude isolated montelukast acid, etc.

The starting amantadine (free base) is either commercially available or may be readily obtained from amantadine hydrochloride. Typically the free base is preferred for forming an amantadine salt of montelukast.

The useful solvents for both salt formation and crystallization of a montelukast amantadine salt include C1-C4 aliphatic alcohols (methanol, ethanol, isopropanol), C2-C6 aliphatic ketones (acetone, methyl isopropyl ketone), C4-C8 aliphatic ethers (diethyl ether, di tert. butyl ether), C4-C6 cyclic ethers (tetrahydrofurane, dioxane), C3-C8 aliphatic esters (ethyl acetate), C5-C8 hydrocarbons (toluene, heptane), C1-C4 chlorinated hydrocarbons (chloroform, dichloromethane), aliphatic C2-C4 nitriles (acetonitrile) and mixtures thereof. The preferred solvent is acetone.

Generally the montelukast is dissolved in the solvent and the solution treated with amantadine. Amantadine may be combined with the montelukast acid solution in a solid state, or, in a dissolved form. The solvent may be the same or different than that used for dissolution of the montelukast acid.

The temperature at which the both solutions are combined may be from the room temperature up to reflux, or the temperature may be increased after the combination of both solutions. The room temperature of the reaction is preferred.

A montelukast amantadine salt precipitates preferably from the reaction mixture spontaneously, but the precipitation may be also induced by cooling, concentrating the solution or adding an antisolvent. Seeds of montelukast amantadine salt may be added to induce or enhance precipitation as well. While the use of an antisolvent, which is commonly described for use in connection with the dicyclohexylamine salt, is possible, it is generally not necessary to achieve suitable yields and purification effect and thus typically avoided.

The precipitated product is isolated from the reaction mixture by conventional separation techniques, e.g. by filtration or centrifugation and is optionally washed and dried. As the filter cake is often quite voluminous, so that the washing would be less effective, it is recommended to suspend it in a suitable amount of the solvent and filter again.

In particular, the salt forming reaction is useful for purification of a crude montelukast acid, i.e. a product having 80% or less content of the title compound. Even such an impure starting material may provide for a solid state amantadine salt, which, after isolation, has a far lower content of side products. Some of the side products present in the crude montelukast acid are well soluble in the solvents useful for the precipitation of the salt; therefore they remain in the mother liquor and are removed/reduced in the desired product. The purification efficacy is comparable to the most convenient amine known so far, the dicyclohexylamine. In particular, the content of less polar impurities decreases dramatically. A simple single treatment of a 70% pure acid may provide for the salt having 85% and higher purity.

The further improvement of the purity may be performed by one or more recrystallizations of the amantadine salt of montelukast from a suitable solvent and/or by converting the formed (and preferably isolated) amantadine salt into montelukast acid and repeating the process of salt formation.

Preferably, a montelukast amantadine salt product having a purity of higher than 95% is obtained, which may be used as an intermediate in making montelukast sodium of pharmaceutical grade. In pharmaceutical applications (which will be discussed later), it is advisable that the purity of the isolated montelukast amantadine salt is 98% and higher, including greater than 99%.

In making montelukast sodium, the isolated amantadine salt may be either converted to the montelukast acid, which is isolated and then converted into montelukast sodium, or it may be converted into the sodium salt directly, via the montelukast acid in the non-isolated state. The later modification is generally more convenient. To do this, the montelukast amantadine salt is typically combined with a solvent system comprising water and a water immiscible organic solvent (e.g., aromatic hydrocarbon such as benzene or toluene, aliphatic hydrocarbon such as hexane or heptane, an aliphatic ester such as ethyl acetate, chlorinated hydrocarbon such as dichloromethane). To this suspension, a water soluble organic acid is added, preferably acetic acid or hydrochloric acid. The organic layer comprising the montelukast acid is then separated. If desired, the montelukast acid may be isolated from this solution, e.g. by removal of the solvent by evaporation or by other known means. Preferably however, such a solution is treated with a source of sodium ion, for instance sodium hydroxide or sodium C1-C4 alkoxide, in an approximately equimolar amount in respect to the montelukast acid. The solution of montelukast sodium is then concentrated and converted into crystalline or amorphous montelukast sodium, as known in the art.

Concerning the second aspect, the known solid state amine salts of montelukast suffer from the disadvantage that the corresponding amine moieties are not pharmaceutically acceptable due to their relatively high toxicity. To the contrary, amantadine salt of montelukast is pharmaceutically acceptable. It may either replace montelukast sodium in its therapeutical regimens, or it may also enhance the therapeutic potential of montelukast per se.

Antiasthmatic drugs are often administered to a human patient by means of an inhalation. By this, the active substance is rapidly absorbed through mucosa, allowing for the desired rapid action of the drug. The montelukast sodium salt is a rather hydrophilic compound and, consequently, it has a low potential to pass the lipid membrane of the mucosal cells. Accordingly, the actually approved medicament comprising montelukast sodium is a tablet for oral administration.

Amantadine salt of Montelukast has improved potential for passing the lipid barrier of the cell membranes due to the lipohilic nature of both parts of the molecule. Thus, it may be more effectively administered via an inhalation route than Montelukast sodium.

The present inventors also suggest that the combination of an antiasthmatic and antiviral drug, combined within a single molecule, will provide a benefit to the asthmatic patients, in particular in comparison with montelukast sodium. Viral infection, and particularly influenza virus infection, may be a serious complication for such type of patients. By administering the compound of the present invention, asthmatic patients will obtain a prophylactic amount of an antiinfluenzal drug, which could minimize the risk of such type of complications. As amantadine has a high potential to accumulate in human blood, even the rather small amounts of amantadine could be beneficial, as they may provide for sufficient plasma levels by accumulation during chronic treatment of the amantadine salt of montelukast.

Therefore, the present invention provides for a pharmaceutical composition comprising the amantadine salt of montelukast and at least one pharmaceutically acceptable carrier and/or excipient. The composition may be adapted for various types of administration. It may be administered orally via a solid dosage form, by inhalation through mucosa, or in an injectable form, for instance. The selection of excipients is dependent on the administration route.

In a tablet form, which is the typical form for oral administration, the composition may comprise excipients such as binders, fillers, disintegrants, lubricants, glidants, etc., and their selection is not particularly restricted. In an injectable form, which may be a liquid form or a freeze-dried powder for reconstitution into solution, the excipients comprise solvents, solubilizers, isotonic agents, buffers, preservatives, etc. Also here the selection of excipients is not particularly restricted.

For administration by inhalation, the compound of the present invention may be delivered in the form of an aerosol spray presentation from pressurized packs or nebulisers. The compound may also be delivered as a powder which may be formulated and the powder composition may be inhaled with the aid of an insufflation powder inhaler device. The preferred delivery system for inhalation is a metered dose inhalation (MDI) aerosol, which may be formulated as a suspension or solution of the composition in suitable propellants, such as fluorocarbons or hydrocarbons. Suitable excipients for formulation of the inhalable composition, if any, are not particularly restricted and are well known in the art.

In making pharmaceutical compositions, montelukast amantadine salt may be used in the crystalline form, preferably as a result of the above manufacturing process. At present, no polymorphic forms of crystalline montelukast amantadine salt have been found, but the formation thereof cannot be excluded. It is also anticipated that montelukast amantadine salt may form hydrates or solvates.

Alternately, the salt may be provided in an amorphous form. A suitable process for making amorphous amantadine salt of montelukast is freeze drying of an aqueous solution of the salt. The amorphous form may be particularly suitable for formulation into the pharmaceutical compositions designed for inhalation route of administration.

EXAMPLES

Example 1

2.5 g of montelukast acid (yellow amorphous solid, purity by HPLC 73.0%) were dissolved in 38 ml of acetone. 1.3 g of 1-aminoadamantane free base were added to the stirred solution at once. Mild brown precipitate was formed after 4-6 min. of intensive stirring. The reaction mixture was stirred for 210 min. at room temperature. Thick precipitate was separated by suction and filter cake was washed with 15 ml of cold acetone (−20° C.). Filter cake was then mixed with 20 ml of acetone and stirred 10 min. at room temperature. The fine precipitate was separated by suction. The filtration cake was washed with 2×15 ml of hexane and dried at room temperature on air.

Yield: 2,05 g of mild grey powder.

HPLC analysis of product: 85.8% of the title compound (relative).

Example 2

2.5 g of montelukast acid (yellow amorphous solid, purity by HPLC 73.0%) were dissolved in 38 ml of acetone. 0.75 g of 1-aminoadamantane was added at once. Brownish precipitate was formed after 6 min of intensive stirring. The reaction mixture was stirred for 220 min. at room temperature. After this period, thick precipitate was sucked off and filter cake was washed with 15 ml of cold acetone (−20° C.). Then filtration cake was subsequently mixed with 20 ml of acetone and stirred for 10 min. at room temperature. The fine precipitate was separated by suction. The filtration cake was washed with 2×15 ml of hexane and dried at room temperature on air.

Yield: 1.95 g of off white powder.

HPLC analysis of product: 88.1% of the title compound (relative).

Example 3

0.3 g of montelukast acid was dissolved in 7 ml of acetone. 0.2 g of 1-aminoadamantane free base was added at once. White precipitate was formed after 5 min of stirring at room temperature. Reaction mixture has thickened so 2.0 ml of cold acetone (−20° C.) were added after 60 min of stirring. The reaction mixture was cooled to 0° C. and precipitate was sucked off. The filtration cake was washed with 2×1 ml of cold acetone and then with 2×5 ml of hexane.

Yield: 0.35 g of white powder.

Example 4

0.7 g of montelukast amantadine salt was stirred in a mixture of 50 ml of water and 15 ml of dichloromethane. Into this heterogeneous system 0.1 ml of 36% HCl was added. Reaction mixture was intensively stirred for 30 min. at room temperature. Layers have been separated and the organic layer was washed with 2×10 ml of dichloromethane. The combined organic layer was extracted with 3×10 ml of water, dried over anhydrous sodium sulphate and concentrated.

Yield 0.54 g (98%) of a yellow solid.

Each of the patents, patent applications, and journal articles mentioned above are incorporated herein by reference. The invention having been described it will be obvious that the same may be varied in many ways and all such modifications are contemplated as being within the scope of the invention as defined by the following claims.

We claim:

1. An amantadine salt of montelukast.
2. A montelukast salt according to formula (4):

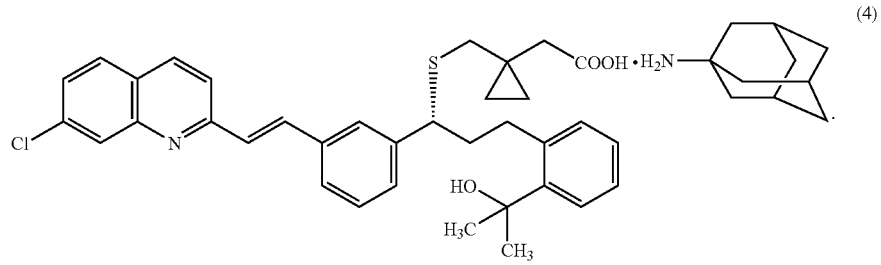

(4)

3. The montelukast salt according to claim 2, in crystalline form.

4. The montelukast salt according to claim 3, wherein said crystalline montelukast salt has a purity of at least 95%.

5. A pharmaceutical composition comprising the montelukast salt according to claim 2 and at least one pharmaceutically acceptable carrier and/or excipient.

6. The pharmaceutical composition according to claim 5, wherein said composition is an inhalable pharmaceutical composition.

7. A process, which comprises:
providing a solution containing montelukast, amantadine, and/or their ions in a solvent; and
crystallizing an amantadine salt of montelukast from said solution.

8. The process according to claim 7, wherein said solvent is selected from the group consisting of C1-C4 aliphatic alcohols, C2-C6 aliphatic ketones, C4-C8 aliphatic ethers, C4-C6 cyclic ethers, C3-C8 aliphatic esters, C5-C8 hydrocarbons, C1-C4 chlorinated hydrocarbons, aliphatic C2-C4 nitriles, and mixtures thereof.

9. The process according to claim 8, wherein said solvent is selected from the group consisting of methanol, ethanol, isopropanol, acetone, methyl isopropyl ketone, diethyl ether, di-tert. butyl ether, tetrahydrofuran, dioxane, ethyl acetate, toluene, heptane, chloroform, dichloromethane, acetonitrile, and mixtures thereof.

10. The process according to claim 9, wherein said solvent is acetone.

11. The process according to claim 7, which further comprises separating said crystalline amantadine salt of montelukast from said solution and, optionally, drying said crystalline amantadine salt of montelukast.

12. The process according to claim 11, which further comprises recrystallizing said crystalline amantadine salt of montelukast.

13. The process according to claim 11, which further comprises converting said amantadine salt of montelukast into montelukast.

14. The process according to claim 13, which further comprises converting said montelukast into sodium montelukast.

15. The process according to claim 7, wherein said solution is provided by adding amantadine or its salt to a crude reaction mixture containing montelukast.

16. A process for purifying montelukast or its salts, which comprises:
synthesizing montelukast in a solution;
adding amantadine to said solution;
precipitating an amantadine salt of montelukast from said solution;
recovering said amantadine salt of montelukast;
optionally recrystallizing said amantadine salt of montelukast from a solvent; and
converting said amantadine salt of montelukast into montelukast or its sodium salt.

17. The process according to claim 16, wherein said conversion of said amantadine salt of montelukast comprises dissolving said amantadine salt of montelukast in an organic solvent and water mixture; treating the mixture with acid; and extracting montelukast using water from the organic phase.

18. The process according to claim 17, wherein said organic solvent is dichloromethane.

19. The process according to claim 16, wherein said solvent used in said recrystallization is acetone.

* * * * *